US012810966B2

(12) United States Patent
Zheng et al.

(10) Patent No.: US 12,810,966 B2
(45) Date of Patent: Nov. 24, 2026

(54) METHOD FOR CONSTRUCTING MOLECULAR FORCE FIELD

(71) Applicant: Divamics Inc., Suzhou City (CN)

(72) Inventors: Zheng Zheng, Beijing (CN); Jianmin Wei, Fuzhou City (CN); Hao Liu, Houma City (CN)

( * ) Notice: Subject to any disclaimer, the term of this patent is extended or adjusted under 35 U.S.C. 154(b) by 460 days.

(21) Appl. No.: 18/401,286

(22) Filed: Dec. 29, 2023

(65) Prior Publication Data

US 2025/0006312 A1 Jan. 2, 2025

Related U.S. Application Data

(63) Continuation-in-part of application No. PCT/CN2023/109117, filed on Jul. 25, 2023.

(30) Foreign Application Priority Data

Jun. 29, 2023 (CN) ......................... 202310787676.9
Oct. 26, 2023 (CN) ......................... 202311399615.1

(51) Int. Cl.
*G16C 10/00* (2019.01)
*G06N 7/01* (2023.01)
*G16B 5/00* (2019.01)
*G16C 20/70* (2019.01)

(52) U.S. Cl.
CPC ............... *G16C 10/00* (2019.02); *G06N 7/01* (2023.01); *G16B 5/00* (2019.02); *G16C 20/70* (2019.02)

(58) Field of Classification Search
CPC .......... G16C 10/00; G16C 20/70; G06N 7/01; G16B 5/00; G16B 15/00; G16B 15/30
See application file for complete search history.

(56) References Cited

U.S. PATENT DOCUMENTS

| | | | | |
|---|---|---|---|---|
| 7,945,396 | B2 | 5/2011 | Fujitani et al. | |
| 10,025,900 | B2 * | 7/2018 | Zanghellini | G16B 20/50 |
| 10,332,616 | B2 * | 6/2019 | Zheng | C40B 30/04 |
| 11,609,807 | B2 | 3/2023 | Chen et al. | |
| 2019/0272468 | A1 * | 9/2019 | Feinberg | G06N 3/02 |

(Continued)

OTHER PUBLICATIONS

Zheng "Generation of Pairwise Potentials Using Multidimensional Data Mining" 2018 <https://pubs.acs.org/doi/pdf/10.1021/acs.jctc.8b00516?ref=article_openPDF> (Year: 2081).*

*Primary Examiner* — Beau D Spratt
(74) *Attorney, Agent, or Firm* — Rahman LLC

(57) ABSTRACT

A method for constructing a molecular force field includes classifying the atomic types and fitting the potential energy function. Initially, atomic types are classified by creating a fingerprint for each atom in the molecular force field, followed by classification using a machine learning clustering method. This one-to-one correspondence between atomic fingerprint and atoms enables the identification of different atomic types. The fitting of the potential energy function employs the BFT (Bayesian field theory) to model atomic ensembles, resulting in a Boltzmann probability distribution for all atoms. Subsequently, a fitting process derives potential energy function parameters from the relationship between probability and energy in the Boltzmann formula. This approach diminishes the molecular force field's reliance on data volume, enhancing computational accuracy.

10 Claims, 9 Drawing Sheets

(56) References Cited

U.S. PATENT DOCUMENTS

| | | | | |
|---|---|---|---|---|
| 2020/0294630 | A1* | 9/2020 | Miller | G16C 20/10 |
| 2021/0375399 | A1* | 12/2021 | Liu | G16C 20/30 |
| 2023/0129485 | A1* | 4/2023 | Pereyaslavets | G16C 20/50<br>703/12 |
| 2023/0273153 | A1* | 8/2023 | Chong | G01N 27/44708<br>204/464 |

* cited by examiner

METHOD FOR CONSTRUCTING MOLECULAR FORCE FIELD

CROSS-REFERENCE TO RELATED APPLICATIONS

The subject application claims priority to Chinese application CN202311399615.1 filed on Oct. 26, 2023 and Chinese application CN202310787676.9 filed on Jun. 29, 2023, and further the subject application is a continuation-in-part of PCT application PCT/CN2023/109117 filed on Jul. 25, 2023, with the PCT application PCT/CN2023/109117 claiming priority to the Chinese application CN202310787676.9 filed on Jun. 29, 2023, the entire contents and subject matter of all these applications thereof being incorporated herein by reference.

FIELD OF INVENTION

The present invention relates to the technical field of structural biology and biomolecular modeling. More specifically, it relates to a method for constructing a molecular force field and a hardware storage device, and a computer system therefor.

BACKGROUND ART

Currently, the atom types in molecular force fields are mostly defined based on empirical knowledge. However, in practical applications, it has been observed that classifying atom types solely based on chemists' knowledge of molecular structures and mathematically describing interatomic energy interaction lacks objectivity and precision. This is due to the inherent limitations of current cognitive levels, which prevents the objective classification of atoms based on their electron density distribution characteristics in various molecular structures. Furthermore, under the computational capabilities of current computers, it is challenging to establish mathematical models for accurate energy calculations of complex target molecular systems.

SUMMARY OF THE INVENTION

The present invention provides a method for constructing a molecular force field. The method mainly includes classifying atom types in the molecular force field and fitting the molecular force field potential function. The classifying of atom types in the molecular force field involves using machine learning methods to cluster fingerprints in the high-dimensional charge density distribution within atoms. This further establishes the atom types in the molecular force field, eliminating the limitations of classifying atom types based on empirical knowledge in traditional molecular force fields and improving the accuracy of the molecular force field. Fitting the molecular force field potential function involves using Bayesian field theory to mine molecular structure data, obtaining the Boltzmann probability distribution among all atoms in each atomic ensemble, fitting the Boltzmann probability, and obtaining the potential parameters of the molecular force field potential function model. This reduces the dependence of the molecular force field on the amount of training data.

Embodiments of the present invention provide:

A method for classifying atom types in a molecular force field, comprising: establishing a molecular force field database; retrieving a target molecule from the molecular force field database and creating a fingerprint for all atoms in the target molecule; clustering the fingerprints of atoms from different elements, wherein the clustering is performed only within the fingerprints of atoms of the same element, thereby achieving classification of atoms and obtaining multiple atom types. The fingerprints establish a one-to-one correspondence with the atoms.

Establishing a molecular force field database is equivalent to preprocessing molecular files. It involves using homology modeling methods to complete missing amino acid residues in protein molecules, using high-precision quantum mechanics methods to calculate partial charges of atoms, and using dynamic methods to bring the molecules to an equilibrium state. The preprocessing of molecular files ensures the quality and accuracy of experimental data and can improve the performance of the molecular force field model.

Preferably, retrieving a target molecule from the molecular force field database involves creating a fingerprint for all atoms in the target molecule. This includes obtaining structural feature and energetic feature of the target molecule, where the structural feature refers to the three-dimensional spatial coordinates of atoms, and the energetic feature refers to the charge distribution of atoms. The total charge distribution of all atoms in the target molecule (Gross Atom Population) is projected onto a Fibonacci lattice constructed for each atom based on different spatial distances to simulate the charge density distribution on the surface of each atom. The energy projection values in the Fibonacci lattice are then sorted and dimensionally reduced to obtain the fingerprint for each atom in the target molecule.

Preferably, clustering is performed on the fingerprints of atoms from different elements. Due to the one-to-one correspondence between atoms and their fingerprints, classification of atoms is achieved, resulting in multiple atom types. This includes using machine learning methods to learn the commonalities and differences in the fingerprints and clustering them accordingly. The clustering results are evaluated to establish classification criteria for the fingerprints of atoms from different elements. Due to the one-to-one correspondence between atoms and their fingerprints, classification of atoms from different elements is achieved, thereby establishing classifying standards for atom types from different elements.

Preferably, in practice, atom types in the molecular force field are classified. If clustering of fingerprints of atoms from different elements results in the formation of new fingerprint types, these new atom types are included in the classifying standards of the molecular force field atom types. Through this approach, the classifying of atom types in the molecular force field is continuously optimized.

A method for fitting a molecular force field potential function comprises: retrieving a complex molecule from the aforementioned molecular force field data; using Bayesian field methods to model the complex molecule and obtain the conditional probability determined by the interaction energy among atoms in the target atomic ensemble of the complex molecule; determining the type of the target atomic ensemble using the aforementioned molecular force field atom type classifying method; fitting the aforementioned conditional probability between any two atoms in the atomic ensemble of that type using a specific potential function model combined with the Boltzmann probability distribution formula.

Preferably, using Bayesian field methods to model the complex molecule and obtain the conditional probability determined by the interaction energy among atoms in the target atomic ensemble of the complex molecule includes: dividing all atoms in the complex molecule into core region atoms and background region atoms; iteratively removing the influence of the probability density distribution of the background region atoms on the core region atoms to obtain the conditional probability among atoms in the atomic ensemble that is solely determined by the interaction energy; the conditional probability satisfies the Boltzmann distribution.

Preferably, determining the type of the target atomic ensemble using the aforementioned molecular force field atom type classifying method; if any atom in the atomic ensemble has a different atom type, then the atomic ensemble has a different type.

Preferably, fitting the aforementioned conditional probability between any two atoms in the atomic ensemble of that type is achieved by using a specific potential function model combined with the Boltzmann probability distribution formula. If the conditional probability satisfies the Boltzmann probability distribution, the relationship between probability and energy can be determined according to the Boltzmann probability formula. By fitting the probability, the potential parameters of the potential function can be determined, and by fitting the Boltzmann probability of each type of atomic ensemble, the potential function between any two atoms in all types of atomic ensemble can be obtained.

In summary, the present invention establishes a molecular force field database. Target molecules are selected from the database, and a fingerprint is created for each atom in the molecule. Clustering is performed on a large number of fingerprints belonging to atoms of the same element, and the clustering results are evaluated. The one-to-one correspondence between atoms and their fingerprints establishes the classification criteria for atom types and further defines the atom types in the molecular force field. Subsequently, complex molecules are retrieved from the molecular force field database. Bayesian field methods are used to model the complex molecules and obtain the conditional probability determined by the interaction energy among atoms in the target atomic ensemble of the complex molecule. The type of the target atomic ensemble is determined using the aforementioned molecular force field atom type classifying method. Since this conditional probability satisfies the Boltzmann distribution, the Boltzmann probability distribution formula is used in conjunction with a specific potential function model to fit the aforementioned conditional probability and obtain the potential function between any two atoms in the atomic ensemble of that type. By integrating all types of potential functions, the molecular force field is obtained.

Optionally, the atomic ensembles include: atom pairs composed of two atoms, or atom groups composed of three atoms. The target molecule is a protein molecule or a ligand small molecule, preferably a protein target molecule or a drug-like small molecule.

Another embodiment of the present invention also provides a computer-readable hardware storage device. The computer-readable hardware storage device stores a computer program that, when executed by a processor, performs the method described above.

Another embodiment of the present invention also provides an electronic device comprising a processor and a memory. The memory stores machine-readable instructions executable by the processor, wherein when the machine-readable instructions are executed by the processor, the method described above is performed.

The electronic device of the present invention can be modularized, comprising: a fingerprint establishment module for establishing a fingerprint for each atom in the target molecule based on the structural feature and energetic feature of the target molecule; an atom type acquisition module for classifying atom types by means of clustering the fingerprints of each type of atom in the target molecule to obtain multiple atom types; a potential energy equation acquisition module for modeling different types of atomic ensembles for each type of atom in the multiple atom types and obtaining the potential energy equations between pairs of atoms in atomic ensembles; and a molecular force field establishment module for establishing a molecular force field based on the potential energy equations of different types of atomic ensembles.

BRIEF DESCRIPTION OF THE DRAWINGS

In order to provide a clearer explanation of the technical solution in the embodiments of the present invention, a brief introduction to the drawings required for the embodiments of the present invention will be given below. It should be understood that the following drawings only illustrate certain embodiments of the present invention, and should not be considered as limiting the scope of the present invention. Those skilled in the art can obtain other related drawings based on these drawings without exercising inventive effort.

The following are descriptions and illustrations of the embodiments of the present invention, as shown in the figures.

EMBODIMENTS

Figure 1:
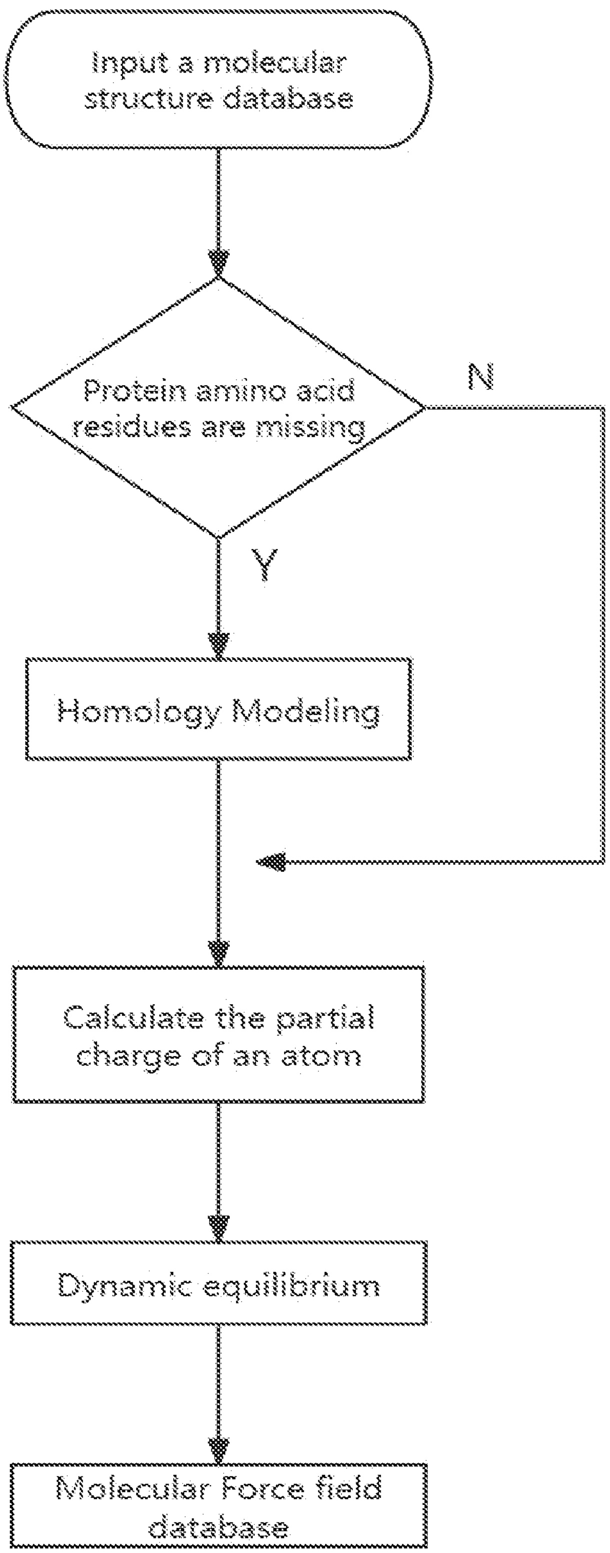
FIG. 1 depicts the schematic diagram of the process for establishing a molecular force field database provided in an embodiment of the present invention.

To make the objectives, technical solutions, and advantages of the present embodiment of the invention clearer, the technical solutions in the present embodiment of the invention will be described clearly and comprehensively in conjunction with the drawings of the present embodiment of the invention. It should be understood that the drawings in the present embodiment of the invention are for illustrative and descriptive purposes only and are not intended to limit the scope of the present embodiment of the present invention. Additionally, it should be understood that the schematic drawings are not drawn to scale. The flowcharts used in the present embodiment of the invention illustrate the operations implemented according to some embodiments of the present embodiment of the invention. It should be understood that the operations in the flowcharts can be implemented in a different order, and steps without a logical context relationship can be reversed or implemented simultaneously. Furthermore, based on the guidance of the embodiments of the present invention, those skilled in the art can add one or more additional operations to the flowcharts or remove one or more operations from the flowcharts.

Additionally, the described embodiments are only a part of the embodiments of the present invention, and not the entirety of the embodiments. The components of the embodiments of the present invention described and illustrated in the accompanying drawings can be arranged and designed in various configurations. Therefore, the detailed description of the embodiments provided in the accompanying drawings is not intended to limit the scope of the present invention as claimed, but merely represents selected embodiments of the present invention.

It is understood that the terms "first" and "second" used in the present invention are used to distinguish similar objects. Those skilled in the art can understand that the terms "first" and "second" do not limit the quantity or execution order, and the terms "first" and "second" do not necessarily indicate that they are different. In the description of the present embodiment of the invention, the term "and/or" is used to describe the relationship between associated objects, indicating that there can be three possibilities, such as A and/or B, which can represent: A exists alone, A and B exist simultaneously, and B exists alone. Additionally, the character "/" in this document generally indicates an "or" relationship between the preceding and following associated objects. The term "multiple" refers to two or more (including two), and similarly, the term "multiple groups" refers to two or more groups (including two groups).

Before introducing the molecular force field modeling method provided in the present invention, some concepts involved in the present invention will be introduced.

A molecular force field is an empirical framework with solid theoretical foundation widely used in computational chemistry and computational biology to simulate the structure and behavior of molecules. It is an empirical potential function that describes the forces and energies in a molecular system by defining the interaction potential among atoms. The basic idea of a molecular force field is to partition the energy of a complex molecular system into a sum of various interacting potentials and introduce mathematical and physical models to describe these interactions. These interactions include bond stretching, angle bending, torsion, electrostatic interactions, van der Waals forces, etc. Typically, a molecular force field assigns specific parameters for each atom type and each bond, angle, torsion, etc., which are fitted based on experimental data, computational results, or information from structural databases.

The structural feature of a molecule refers to the information required to determine the structure of a molecular system. This information typically includes the positions of atoms, the types and lengths of chemical bonds, and the geometric configuration of the molecule. The structural feature of a molecule is the foundation for molecular dynamics, simulation, and computation, and is crucial for understanding the structure, properties, and functions of molecules.

The energetic feature of a molecule refers to information that describes the energy of a molecular system, including the total energy of the molecule, kinetic energy, potential energy, and intra-molecular interaction energy. The energetic feature of a molecule is the foundation for understanding the stability of molecules, reaction kinetics, photochemical reactions, and spectroscopy, among other chemical processes.

Clustering refers to the process of dividing multiple character sequences into multiple classes composed of similar character sequences based on one or more dimensions. In other words, the ensembles generated by clustering are a collection of data objects that are similar to each other within the same ensemble and different from objects in other ensembles.

Bayesian Field Theory (BFT), also known as Bayesian networks, is one of the most effective theoretical models in the field of uncertain knowledge representation and inference. Bayesian networks use directed edges to express the relationships between nodes, providing stronger semantics and powerful tools for studying the conditional probability distribution of geometric structures of atomic pairs'. Bayesian Field Theory is a variant method of Bayesian networks, which makes the following assumptions: the entire molecular system is divided into a core region and a background region, where the core region consists of a ensemble of target atoms, and the background region includes the remaining part of the molecule except for the core region. Atoms in the background region can only directly interact with the target atomic ensemble through neighboring atoms, while other atoms can only indirectly interact with the target atomic ensemble through these neighboring atoms. All indirect interactions are considered as background nodes, and all interactions that affect the target atomic ensemble in the system are propagated through background chains (background node, neighboring atom node, target atomic ensemble). The background chains form a Markov chain, where the current node is only influenced by the previous node, and the background chains are independent of each other.

The Boltzmann probability distribution is a mathematical model used to describe the distribution of particles in a thermodynamic system. It can be used to represent the probability of the system being in a specific state, which is related to its energy. The expression for Boltzmann probability is as follows:

$$P = \frac{1}{Z} e^{-\frac{E}{kT}}$$

where Z is the partition function, k is the Boltzmann constant, and T is the temperature of the system. This formula explains that in a state of thermal equilibrium, the relative probability of each state in the system is related to its energy. States with lower energy have a higher probability, while states with higher energy have a lower probability. This is consistent with intuitive understanding because in a state of thermal equilibrium, the system tends to occupy states with lower energy.

It should be noted that the molecular force field modeling method provided in the present invention can be executed by electronic devices. Here, electronic devices refer to device terminals or servers with the capability to execute computer programs. Examples of device terminals include smartphones, personal computers, tablets, personal digital assistants, or mobile internet devices. Servers refer to devices that provide computing services through a network, such as x86 servers and non-x86 servers. Non-x86 servers include mainframes, minicomputers, and UNIX servers.

The present invention discloses a method for classifying molecular force field atom types, including: establishing a molecular force field database; obtaining target molecules from the molecular force field database and creating fingerprint patterns for all atoms in the target molecules; clustering the fingerprint patterns of atoms of different elements, which allows for the classification of atoms based on their fingerprint patterns, resulting in multiple atom types. The clustering is only performed within the fingerprint patterns of atoms of the same element.

As shown in FIG. 1, protein molecules, ligand molecules, and complex molecules are first obtained from a molecular structure database. Homology modeling methods are used to complete protein molecules with missing amino acid residues. High-precision quantum mechanical methods are used to calculate partial charges of atoms, and dynamic methods are used to bring the molecules to an equilibrium state.

Amino acid residue loss occurs when high-resolution structures in the molecular structure database are obtained through protein crystallization. Some amino acid residues may not be resolved or captured by the model, resulting in their absence in the structure file. This may be due to factors such as crystallization conditions and the quality of the crystal.

Homology Modeling, also known as comparative modeling, is a computational method used to predict protein structures. It is based on the assumption of homology, which states that proteins with similar sequences also have similar structures. This method is typically used when the structure of the target protein has not been resolved, but there are known proteins with similar structures.

Furthermore, high-precision quantum mechanical methods are used to calculate the partial charges of atoms. Partial charges of atoms refer to the contribution of the charge distribution of the electron cloud in an atom to the overall charge of the atom. In molecular or crystal structures, atoms are typically considered as a positively charged atomic nucleus surrounded by negatively charged electron clouds.

Moreover, dynamic methods are used to bring the molecules to an equilibrium state. Dynamic equilibrium ensures that the simulated system reaches a state of physical equilibrium within the simulation time. This means that the macroscopic and microscopic properties of the system, such as temperature, pressure, and energy distribution, tend to stabilize, resulting in simulation results that are closer to the behavior of the real system.

Establishing a molecular force field database is equivalent to preprocessing the molecular files. Preprocessing the molecular files ensures the quality and accuracy of experimental data and can improve the performance of the molecular force field model.

Figure 2:
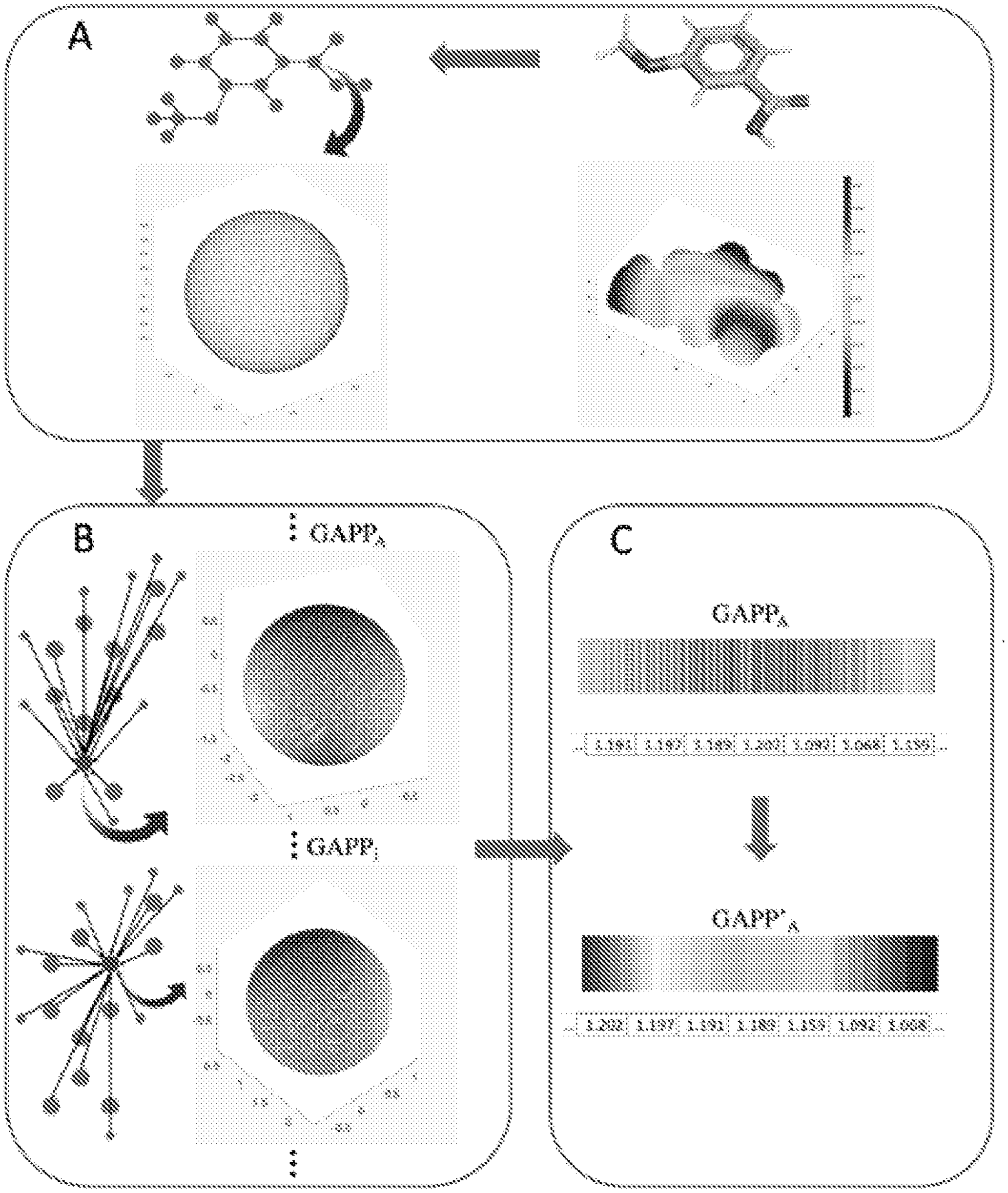
FIG. 2 illustrates the steps for establishing atomic fingerprints provided in an embodiment of the present invention.

As shown in FIG. 2, preferably, target molecules are obtained from the molecular force field database, and fingerprint patterns are established for all atoms in the target molecules. This includes obtaining structural feature and energetic feature of the target molecules. The structural feature refers to the three-dimensional spatial coordinates of atoms, while the energetic feature refers to the charge distribution of atoms. The total charge distribution of all atoms in the target molecules (Gross Atom Population) is projected onto a Fibonacci sphere lattice constructed for each atom based on different spatial distances to simulate the charge density distribution on the surface of each atom. The energy projection values in the Fibonacci sphere lattice are then sorted in a dimension-reducing manner to obtain the fingerprint patterns for each atom in the target molecules.

In the implementation process of the above scheme, by extracting information from the files, the structural feature and energetic feature of the target molecules can be obtained more effectively. This avoids the time and resource consumption of conducting experiments or computational simulations, thereby improving the efficiency and accuracy of determining the charge distribution.

The Fibonacci sphere lattice is a sampling method for uniformly distributing points on a spherical surface. The points on the Fibonacci sphere have fixed three-dimensional coordinates, allowing us to directly represent the three-dimensional coordinates using the index of the Fibonacci sphere points, thereby achieving dimension reduction from three-dimensional to one-dimensional. Since the global configuration of the molecule does not need to be considered, it improves the speed of processing molecular structures and properties.

In FIG. 2, (A) the Fibonacci sphere lattice is generated on the surface of each atom in the molecule using the structural feature and energy information extracted from the molecular file; (B) the total charge distribution of each atom in the molecule is projected onto each point of the Fibonacci sphere lattice; (C) the Fibonacci sphere sequence is sorted in a dimension-reducing manner to obtain the fingerprint patterns for each atom.

Preferably, the fingerprint patterns of atoms of different elements are clustered to achieve classification of atoms based on the one-to-one correspondence between atoms and their fingerprint patterns, resulting in multiple types of atoms. This includes using machine learning methods to learn the commonalities and differences of the fingerprint patterns and cluster them accordingly. The clustering results are then evaluated to establish classification criteria for the fingerprint patterns of atoms of different elements. Due to the one-to-one correspondence between atoms and their fingerprint patterns, the classification of atoms of different elements is achieved, thereby establishing defined standards for different types of atoms of different elements.

The classifying of atom types in traditional molecular force fields is based on the understanding of molecular structures by structural chemists. For example, the AMBER molecular force field classifies atom types based on the element type of the atom, the hybridization type of the atom, and the position of the atom in the molecular structure. This classification method is not objective enough and not efficient, as the presence of cognitive barriers makes it difficult to discover some atom types using human intuition based on existing experience. This patent proposes a method for constructing atom fingerprint patterns based on the charge distribution on the atom surface. Based on this, a set of atom type classification methods is established by combining machine learning clustering methods and classification evaluation methods. Even for ligand small molecules in complex chemical environments, this method can quickly and accurately perform classification tasks. Table 1 shows the differences in the number of atom classifications for different elements between the present invention and the AMBER molecular force field.

TABLE 1

| element | H | C | N | O | S | Total |
|---|---|---|---|---|---|---|
| The number of atom type classifications in the present invention (total number = protein + ligand) | 23 = 11 + 12 | 26 = 13 + 13 | 14 = 7 + 7 | 14 = 7 + 7 | 4 = 3 + 1 | 81 |
| Number of atom type classifications in existing technologies (mainstream molecular force fields such as AMBER/GARF) | 12 | 13 | 7 | 5 | 2 | 39 |

From the table, it can be seen that the number of atom classifications in this invention is significantly higher than some existing mainstream molecular force fields. The AMBER molecular force field has increased its number of atom classifications in subsequent versions, improving the performance of the molecular force field. This also serves as evidence that the existing molecular force field atom type classifying based on human experience does not classify all atom types.

Preferably, in practice, the aforementioned multiple types of atoms are used to form a standard atom database. If atoms of different elements are clustered to form new atom types, these new atom types are included in the standard atom database. Through this approach, the standard atom database is continuously optimized and improved. For example, if there are 7 types of oxygen atoms in the standard atom database and a new type of oxygen atom is added, the total number of oxygen atom types in the standard atom database becomes 8. This method is used to update the standard atom database based on the actual classification situation.

And a fitting method for a molecular force field potential function, comprising: obtaining a complex molecule from the aforementioned molecular force field data; modeling the complex molecule using a Bayesian field method to obtain the conditional probability of the interaction energy among atoms in the target atomic ensemble in the complex molecule; determining the type of the target atomic ensemble using the aforementioned molecular force field atom type classifying method; fitting the aforementioned conditional probability using a specific potential function model combined with the Boltzmann probability distribution formula to obtain the potential function between any two atoms in the atomic ensemble of that type.

Preferably, the complex molecule is modeled using a Bayesian field method to obtain the conditional probability of the interaction energy among atoms in the target atomic ensemble in the complex molecule, including: dividing all atoms in the complex molecule into core region atoms and background region atoms; iteratively removing the influence of the probability density distribution of the background region atoms on the core region atoms to obtain the conditional probability solely determined by the interaction energy among atoms in the atomic ensemble; the conditional probability satisfies the Boltzmann distribution.

Preferably, the type of the target atomic ensemble is determined using the aforementioned molecular force field atom type classifying method. If the atom type of any atom in the atomic ensemble is different, then the type of the atomic ensemble is different.

Preferably, the aforementioned conditional probability is fitted using a specific potential function model combined with the Boltzmann probability distribution formula to obtain the potential function between any two atoms in the atomic ensemble of that type. If the conditional probability satisfies the Boltzmann probability distribution, then the relationship between probability and energy can be determined according to the Boltzmann probability formula. Fitting the probability allows for the determination of the potential parameters of the potential function, and fitting the Boltzmann probability of each type of atomic ensemble enables the determination of the potential function between any two atoms in all types of atomic ensembles.

In summary, the present invention establishes a molecular force field database. From the database, a target molecule is selected, and a fingerprint is created for each atom in the molecule. The fingerprints belonging to atoms of the same element are clustered, and the clustering results are evaluated. The one-to-one correspondence between atoms and their fingerprints establishes the classification criteria for atom types, and further classifies the atom types for the molecular force field. Subsequently, complex molecules are obtained from the molecular force field database. The complex molecules are modeled using the Bayesian field method to obtain the conditional probability of the interaction energy among atoms in the target atomic ensemble in the complex molecule. The type of the target atomic ensemble is determined using the aforementioned molecular force field atom type classifying method. Since the conditional probability satisfies the Boltzmann distribution, the Boltzmann probability distribution formula is used in conjunction with a specific potential function model to fit the aforementioned conditional probability and obtain the potential function between any two atoms in the atomic ensemble of that type. Integrating all types of potential functions yields the molecular force field.

Embodiment 1

Figure 3:
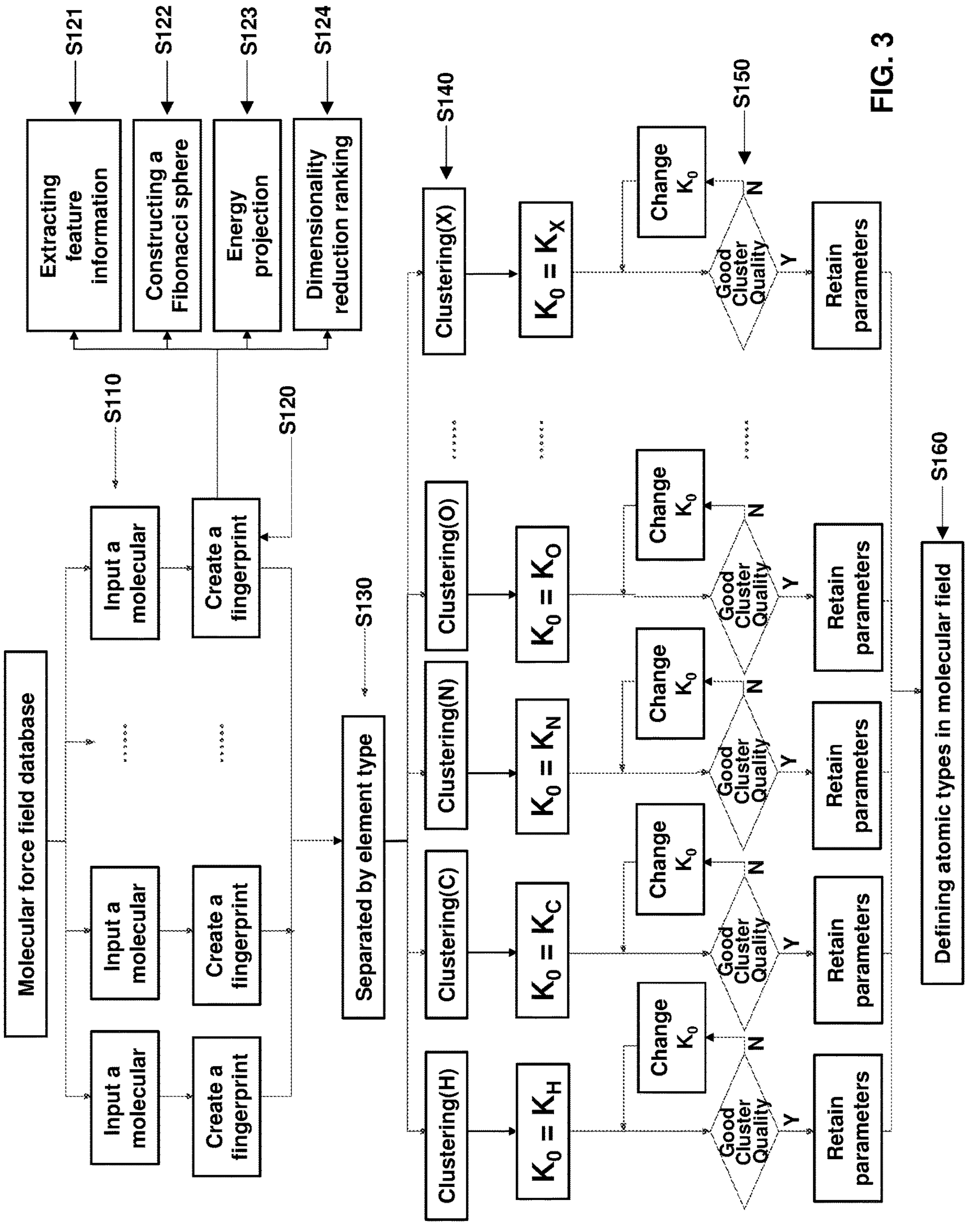
FIG. 3 depicts the schematic diagram of the process for classifying atomic types in the molecular force field provided in an embodiment of the present invention.

Referring to the schematic diagram of the molecular force field atom type classifying process shown in FIG. 3 of the present invention embodiment, the present invention embodiment provides a method for classifying molecular force field atom types, comprising:

Step S110: Retrieve standard molecular files from the molecular force field database.

The format of the standard molecular files includes, but is not limited to, pdb, mol2, sdf, and the molecular types are protein molecules or ligand small molecules. Preferred molecular types are drug target protein molecules or drug-like small molecules.

The above-mentioned standard molecular files are mainly obtained from the established molecular force field database.

In case of reducing the standards, commonly used molecular structure databases such as PDB, BMRB, and others can also be directly used for retrieving molecular files.

Step S120: Establish a fingerprint spectrum for each atom of the retrieved molecules.

It can be understood that different atoms have different fingerprint spectra, and each atom corresponds to its own fingerprint spectrum. The fingerprint spectrum can be used to identify and differentiate different atoms.

Step S130: Classify the fingerprint spectra based on the different elemental types of the atoms.

It can be understood that the classification of molecular force field atom types is only performed within atoms of the same elemental type. Therefore, the processing of fingerprint spectra is also performed only within atoms of the same elemental type.

Step S140: Use machine learning clustering methods to cluster the fingerprint spectra for each elemental type.

In the specific implementation process, machine learning clustering methods can include the K-means clustering algorithm, K-means++, or artificial neural network algorithms. Taking K-means++ as an example, K-means++ is an optimized algorithm for K-means clustering. Compared to K-means, which randomly selects K initial cluster centers, K-means++ only randomly selects the first initial cluster center, effectively avoiding clustering getting stuck in local minima. Similar to K-means, before clustering, the number of desired clusters K needs to be predetermined. In this case, we can choose the number of classifications in AMBER as the initial K value.

Step S150: Evaluate the clustering results.

Taking the example of using K-means++ clustering in Step S140, the silhouette coefficient method can be used to evaluate the clustering results. The evaluation criteria are as follows: (1) Silhouette coefficient S>0.9; (2) The number of samples in the cluster with the fewest samples after clustering is not less than 5% of the total number of samples. If the evaluation criteria are not met, the K value is changed and the process returns to Step S140. If the evaluation criteria are met, the relevant parameters of the clustering in Step S140 are retained for the next step.

Step S160: Classify molecular force field atom types.

It can be understood that after clustering, relevant parameters of the clustering can be obtained. Taking K-means++ clustering as an example, these parameters include the number of clusters K and the coordinates of each cluster center. Using these parameters, samples of the same type can be classified outside of the clustered samples. Therefore, we can use the clustering-related parameters retained in Step S150 to classify the fingerprint spectra of atoms and thus classify atom types.

As an optional embodiment of the above Step S120, fingerprint spectra are established for each atom of all obtained molecules. This includes:

Step S121: Extracting structural feature and energetic feature of the molecules.

Structural feature includes, but is not limited to, the three-dimensional coordinates of each atom in the molecule, which can be directly obtained from standard molecular files. Energetic feature includes, but is not limited to, the proton charge and partial charge of each atom in the molecule. The proton charge can also be directly obtained from standard files, while the partial charge can be calculated using a combination of quantum mechanical methods and empirical methods, such as the RESP (Restrained Electro Static Potential) method and the AM1-BCC (AM1-Bond Charge Correction) method.

Step S122: Construct a Fibonacci lattice on the surface of each atom in the molecule.

It can be understood that we consider the atom as a uniform sphere. The Fibonacci lattice is a sampling method that achieves uniform point sampling on a spherical surface. The three-dimensional coordinates of the nth point in the lattice are given as follows:

$$x_n = \sqrt{1 - z_n^2} \cdot \cos(2\pi n\phi)$$

$$y_n = \sqrt{1 - z_n^2} \cdot \sin(2\pi n\phi)$$

$$z_n = \frac{(2n-1)}{N} - 1$$

where N is the total number of points in the Fibonacci lattice, and in this patent, N is set to 1000. $\phi$ represents the golden ratio.

Step S123: Project the total charge distribution of each atom in the molecule onto each point of the Fibonacci lattice to simulate the charge density distribution on the surface of each atom.

The relationship between the total charge distribution (Gross atom population) and the atomic number Z, as well as the partial charge Q, is as follows:

$$Q = Z - GAP$$

Where the atomic number Z is numerically equal to the proton charge of the atom.

In the specific implementation process, the projection can be done using a Gaussian-type basis set. In quantum chemistry, a basis set is a set of functions used to describe the wave function of a system. Gaussian-type basis sets use Gaussian functions as the core, and the projection formula for point $\alpha$ in the Fibonacci lattice is given as follows:

$$GAPP_\alpha = \sum_i^M GAPP_{i-\alpha}(R_{i-\alpha}, GAP_i) = \sum\nolimits_i^M GAP_i \cdot \exp\left(-\frac{\pi (GAP_i)^{\frac{4}{3}}}{2} |R_{i-\alpha}|^2\right)$$

Step S124: Perform dimensionality reduction and sorting on the charge density distribution on the surface of each atom in the molecule to obtain a fingerprint spectrum for each atom in the target molecule.

It can be understood that the Fibonacci lattice is an ordered three-dimensional lattice with indices. Therefore, replacing the three-dimensional coordinates with a one-dimensional index can achieve the purpose of dimensionality reduction.

Embodiment 2

Figure 4:
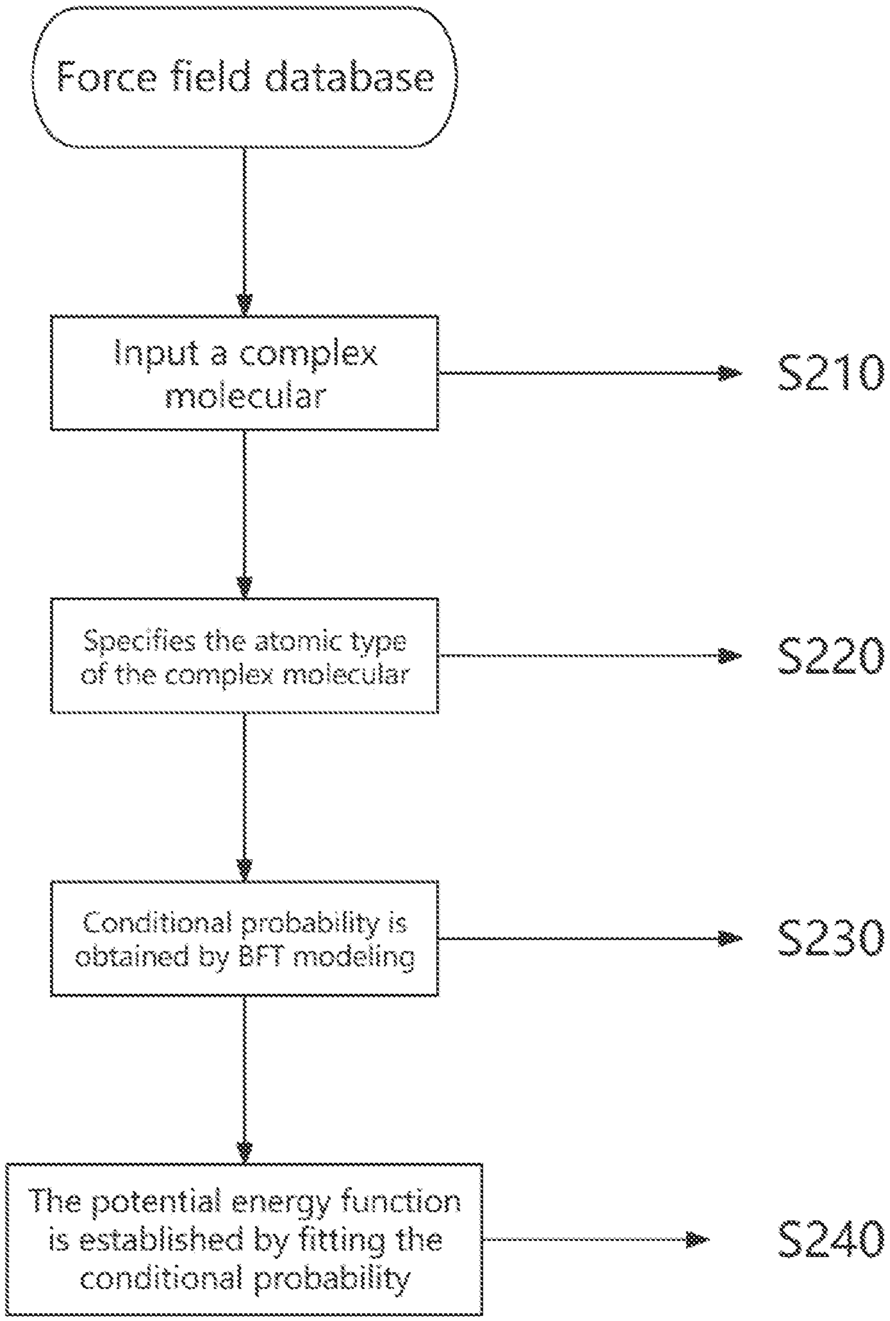
FIG. 4 illustrates the schematic diagram of the process for fitting the potential energy function of the molecular force field provided in an embodiment of the present invention.

Please refer to FIG. 4, which illustrates the schematic diagram of the process for fitting the potential energy function of the molecular force field provided in the embodiments of the present invention, including:

Step S210: Retrieve complex molecules from the molecular force field database.

Complex molecules refer to interacting receptor-ligand molecules, and these complex molecules can be protein-ligand molecules. Preferably, the complex molecules consist of drug target proteins and ligand-like small molecules.

Step S220: Use the aforementioned method for classifying atomic types to classify the atomic types of atoms in the complex molecule.

It can be understood that classifying the atomic types of atoms implies the simultaneous determination of the types of atomic ensembles. If the atomic type of any atom in an atomic ensemble is different, the type of the atomic ensemble is considered different.

Step S230: Model the complex molecule using Bayesian field theory, obtaining the conditional probability between any two atoms in atomic ensembles of different types, influenced only by their interaction energy.

It can be understood that Bayesian field theory, as a variant of Bayesian networks, makes the following conventions: the entire molecular system is divided into a core zone and a background zone, where the core zone represents the target atomic ensemble, and the background zone comprises the portion of the molecule excluding the core zone. Atoms in the background zone can directly interact with the target atomic ensemble only if they are neighboring atoms of the target atomic cluster. Other atoms can only exert indirect interactions on the target atomic cluster through the aforementioned neighboring atoms. All indirect interactions are considered background nodes, and interactions affecting the target atomic cluster propagate through background chains (background node→neighboring atom node→target atomic ensemble). The background chains form a Markov chain, where the current node is only influenced by the previous node, and the background chains are mutually independent.

It can be understood that the particles in this conditional probability statistics are particles in a state of thermal equilibrium, and therefore, this conditional probability follows the Boltzmann distribution.

Step S240: Use a specific potential function model combined with the Boltzmann probability distribution formula to fit the above conditional probability, obtaining the potential function between any two atoms in atomic ensembles of that type.

In the specific practical process, we can choose the following potential function model:

$$E(r)=\varepsilon\left[\left(\frac{\sigma}{r}\right)^{\alpha}-\left(\frac{\sigma}{r}\right)^{\beta}\right]$$

In this case, the atomic distance r serves as the independent variable, α, β, ε and σ are potential parameters (α is the attraction coefficient, β is the repulsion coefficient, ε is four times the potential well depth, and σ is the distance between the two atoms corresponding to the potential energy minimum.). Due to the aforementioned conditional probability following the Boltzmann distribution, combining it with the Boltzmann formula, we can establish the relationship between the conditional probability and the potential parameters:

$$P(r)=e^{-\frac{\varepsilon\left[\left(\frac{\sigma}{r}\right)^{\alpha}-\left(\frac{\sigma}{r}\right)^{\beta}\right]}{RT}}$$

Fit the aforementioned conditional probability to obtain the potential parameters of the potential function, thereby establishing the potential energy function corresponding to the statistically derived conditional probabilities for that type of atomic ensemble.

As an optional implementation of the above step S230, modeling the complex molecule using Bayesian field theory to obtain the conditional probability between any two atoms in atomic ensembles of different types, influenced only by their interaction energy, can include:

Step S231: Introduce Bayesian networks to generate a mapping diagram for the molecular system.

Figure 5:
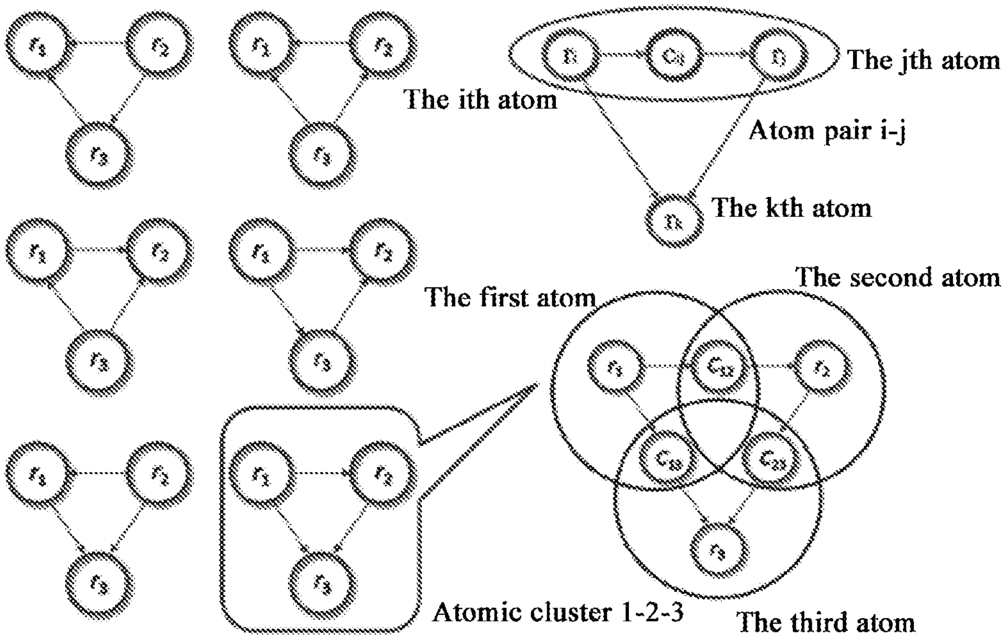
FIG. 5 depicts the directed acyclic graphs for atomic pairs composed of two atoms and atomic groups composed of three atoms provided in an embodiment of the present invention.

It can be understood that Bayesian networks use directed edges to indicate variable dependencies and are effective tools for studying the probability distribution of atomic geometric properties. According to the definition, a Bayesian network is a Directed Acyclic Graph (DAG), having directed edges but no directed cycles. For a DAG of a molecule, only two conditions need to be satisfied: (1) there are pairwise interactions between any two atoms in the molecular system, in other words, there are no isolated nodes in the molecular graph network; (2) at a specific equilibrium state, the number of particles and the number/types of pairwise contacts in a molecular system remain constant. This allows the use of a Bayesian network to model the molecular system. FIG. 5 illustrates the directed acyclic graphs for atomic pairs and atomic groups composed of two and three atoms, respectively, provided in the embodiments of the present invention.

Figure 6:
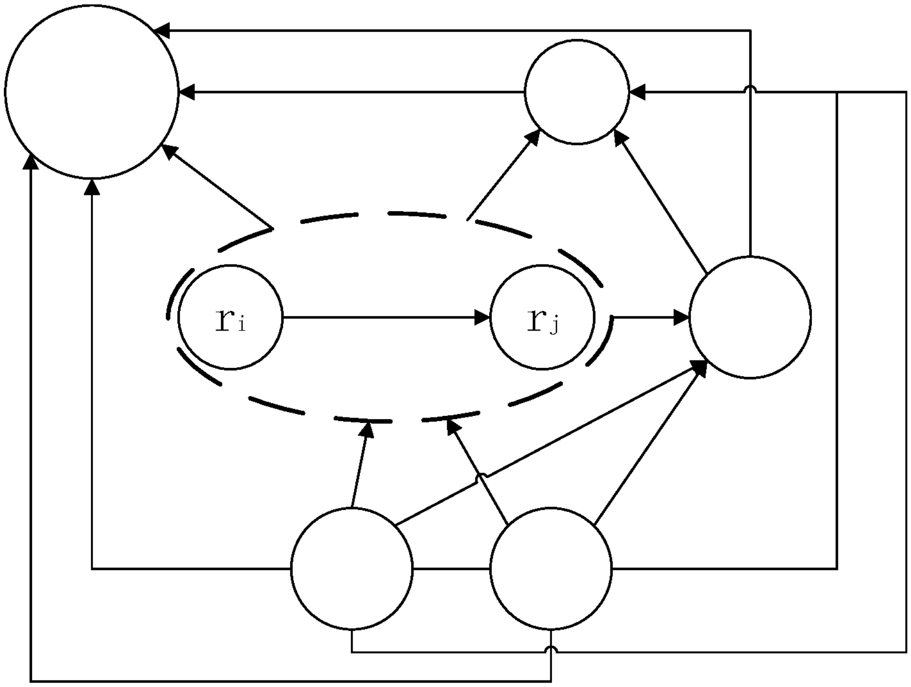
FIG. 6 illustrates the molecular network mapping diagram provided in an embodiment of the present invention.

Please refer to FIG. 6 for the molecular network mapping diagram. In the specific practical process, taking the atomic pair i-j (ellipse in the diagram) as the research object. The nodes of the Bayesian network (circles in the diagram) are divided into two categories: atomic coordinate nodes r and atomic pairwise interaction nodes c. The arrowed lines in-between nodes indicate the connection between atomic interactions and atomic coordinates. The likelihood can be obtained from the Bayesian probability formula:

$$P(c_{ij}\mid r_i,r_j)=\frac{P(r_i,r_i\mid c_{ij})P(r_i,r_j)}{P(c_{ij})}\propto P(r_i,r_j\mid c_{ij})$$

Where $P(c_{ij}|r_i, r_j)$ represents the likelihood probability between the atomic pair i-j, $P(c_{ij})$ is the prior probability of whether there is interaction between the atomic pair i-j, and this prior probability is 1 when there is an interaction between the atomic pair i-j, and 0 when there is no interaction between the atomic pair i-j. $P(r_i, r_j)$ represents the non-conditional probability distribution of the atomic pair i-j under unconstrained conditions. The ultimate modeling goal $P(r_i, r_j|c_{ij})$ is to determine the conditional probability that the two atoms in the atomic pair i-j are influenced only by their interaction energy.

As the above conditional probability is inherently a function of the distance between two atoms, it can be represented using an interaction distance node dij instead of atomic coordinate nodes ri and rj, $P(r_i, r_j|c_{ij})$ can be rewritten as $P(d_{ij}|c_{ij})$. According to the chain rule of probability, the molecular network shown in FIG. 6 can be represented as follows:

$$P(c_{ij},d_{ij}\mid C,r)=\frac{P(C,R\mid c_{ij},d_{ij})P(c_{ij},d_{ij})}{P(C,R)}=\frac{P(c_v,r_v,c_{v+1},r_{v+1},c_{v+2},r_{v+2},\ldots,c_n,r_n\mid c_{ij},d_{ij})P(d_{ij}\mid c_{ij})P(c_{ij})}{P(c_v,r_v,c_{v+1},r_{v+1},c_{v+2},r_{v+2},\ldots,c_n,r_n)}$$

Here, C is the set of all pairwise interactions in the target molecular system, R is the set of all atomic coordinate nodes in the target molecular system, and v is the index of the nearest node to the target atomic pair among the distance nodes or interaction nodes.

It can be understood that in the molecular network, each atom is involved in multiple interactions, and atoms of different types will be connected in different ways. Since the interactions of the target atomic pair cannot be quantified independently, training a model using such a complex structure would result in the "curse of dimensionality." Therefore, it is necessary to introduce Bayesian field theory to simplify the molecular graph model.

Step S232: Simplify the molecular network using Bayesian field theory.

Figure 7:
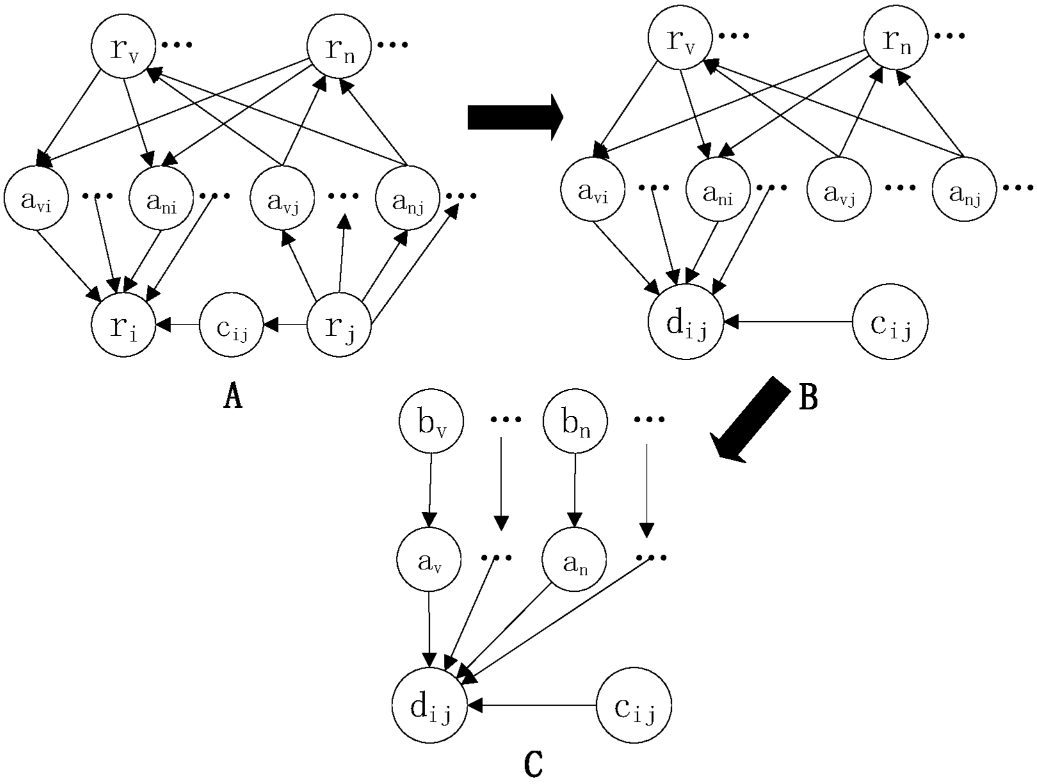
FIG. 7 depicts the schematic diagram of the process for simplifying molecular networks using BFT provided in an embodiment of the present invention.

Please refer to FIG. 7, illustrating the process of simplifying the molecular network using Bayesian Field Theory (BFT) in the embodiments provided by the present invention. Although in the molecular network, there are interactions between any two atoms, and any atom in the background region can affect atoms in the core region, it can be understood that the influence of atoms in the background region on atoms in the core region decreases with increasing distance. The bonding interactions of neighboring atoms are much greater than other interactions. Therefore, BFT makes the following agreement: in the molecular graph network, only adjacent atomic nodes in the background region are directly connected to the atomic nodes in the core region. while other nodes can only be indirectly connected to nodes in the core region by connecting to the aforementioned neighboring atom nodes.

Subgraph A illustrates the relationship between the core region nodes ri-cij-rj, neighboring atom node a and background region atom coordinate nodes r. Due to the inherent nature of the molecular force field potential function being a function of the distance between two atoms, Subgraph B uses an interaction distance node dij to replace the atomic coordinate nodes ri and rj. It also indicates that BFT makes the following agreement: the interaction among target atoms in the core region is independent of the impact on the core region from interactions involving atom pairs in the background region. Subgraph C uses background node b to describe all indirect interactions from the entire background region to the core region through adjacent atoms. This indicates that BFT makes the following agreement: all interactions in the molecular system that affect the target atomic ensemble propagate through the background chain (background node adjacent atom node target atomic ensemble); the background chain is a Markov chain, where the current node is only influenced by the previous node, and the background chains are independent of each other. In the BFT-simplified molecular network, the conditional probability of any two atoms forming a target atom pair can be expressed as follows:

$$P(r_i, r_j \mid c_{ij}, C, R, B) =$$
$$P(d_{ij} \mid c_{ij})P(d_{ij} \mid C, R, B) = P(d_{ij} \mid c_{ij})\prod_m^{N_v} P(d_{ij} \mid c_m, r_m, b_m) =$$
$$P(d_{ij} \mid c_{ij})\prod_m^{N_v} P(d_{ij} \mid c_m)P(c_m \mid r_m)P(r_m \mid b_m) \propto$$
$$P(d_{ij} \mid c_{ij})\prod_m^{N_v} P(d_{ij} \mid c_m)P(r_m \mid c_m)P(r_m \mid b_m)$$

Here, m represents the index of the interaction path, and Nv represents the total number of interaction paths.

Similarly, in the BFT-simplified molecular network, the conditional probability of any three atoms forming the target atom group can be expressed as follows:

$$(r_i, r_j, r_k \mid c_{ijk}, C, R, B) = P(d_{ij}, d_{ik}, d_{jk} \mid c_{ijk})P(d_{ij}, d_{ik}, d_{jk} \mid C, R, B) =$$
$$P(d_{ij}.d_{ik}, d_{jk} \mid c_{ijk})\prod_m^{N_v} P(d_{ij}, d_{ik}, d_{jk} \mid c_m, r_m, b_m) =$$
$$P(d_{ij}, d_{ik}, d_{jk} \mid c_{ijl})\prod_m^{N_v} P(d_{ij}, d_{ik}, d_{jk} \mid c_m)P(c_m \mid r_m)P(r_m \mid b_m) \propto$$
$$P(d_{ij}, d_{ik}, d_{jk} \mid c_{ijl})\prod_m^{N_v} P(d_{ij}, d_{ik}, d_{jk} \mid c_m)P(r_m \mid c_m)P(r_m \mid b_m)$$

Step S233: Subtract the impact of background chains on the core region to obtain the conditional probability of any two atoms in various types of atomic ensembles influenced solely by their interaction energy.

Modeling with the m-th background chain's atomic coordinate node rm as the target variable, interaction node cm, background node bm, and atomic pair distance node dij as conditional variables, $P(r_m|c_m, b_m, d_{ij})$ can be expressed as follows:

$$P(c_m \mid r_m, b_m, d_{ij}) = P(c_m, d_{ij} \mid r_m)P(r_m \mid b_m) =$$
$$\frac{P(r_m \mid c_m, d_{ij})P(c_m, d_{ij})}{P(r_m)}P(r_m \mid b_m) \propto P(r_m \mid c_m)P(d_{ij} \mid c_m)P(r_m \mid b_m)$$

Where $P(r_m|c_m)P(d_{ij}|c_m)P(r_m|b_m)$ represents the influence of the m-th action path on the target atomic ensemble. By dividing the formula from step S232 by the above equation, iteratively removing the probability density distribution effect of background atomic pairs on the core atomic pairs, $P(d_{ij}|c_{ij})$, the conditional probability only affected by their mutual interaction energy between any two atoms in the atomic ensemble is obtained:

$$\frac{P(d_{ij} \mid c_{ij}, C, R, B)}{\prod_m^{N_v} P(r_m \mid c_m, b_m, d_{ij})} = \frac{P(d_{ij} \mid c_{ij})\prod_m^{N_v} P(d_{ij} \mid c_m)P(r_m \mid c_m)P(r_m \mid b_m)}{\prod_m^{N_v} P(r_m \mid c_m, b_m, d_{ij})} \propto$$
$$\frac{(d_{ij} \mid c_{ij})\prod_m^{N_v} P(d_{ij} \mid c_m)P(r_m \mid c_m)P(r_m \mid b_m)}{\prod_m^{N_v} P(r_m \mid c_m)P(d_{ij} \mid c_m)P(r_m \mid b_m)} = P(d_{ij} \mid c_{ij})$$

Similarly, $P(d_{ij}, d_{ik}, d_{ik}|c_{ijk})$, the conditional probability affected only by their common interaction energy among any three atoms in the atomic ensemble can be derived:

$$\frac{P(d_{ij}, d_{ik}, d_{jk} \mid c_{ijk}, C, R, B)}{\prod_m^{N_v} P(r_m \mid c_m, b_m, d_{ij}, d_{ik}, d_{jk})} =$$
$$\frac{P(d_{ij} \mid c_{ij})\prod_m^{N_v} P(d_{ij}, d_{ik}, d_{jk} \mid c_m)P(r_m \mid c_m)P(r_m \mid b_m)}{\prod_m^{N_v} P(r_m \mid c_m, b_m, d_{ij}, d_{ik}, d_{jk})} \propto$$
$$\frac{(d_{ij}, d_{ik}, d_{jk} \mid c_{ij})\prod_m^{N_v} P(d_{ij}, d_{ik}, d_{jk} \mid c_m)P(r_m \mid c_m)P(r_m \mid b_m)}{\prod_m^{N_v} P(r_m \mid c_m)P(d_{ij}, d_{ik}, d_{jk} \mid c_m)P(r_m \mid b_m)} =$$
$$P(d_{ij}, d_{ik}, d_{jk} \mid c_{ijk})$$

Figure 8:
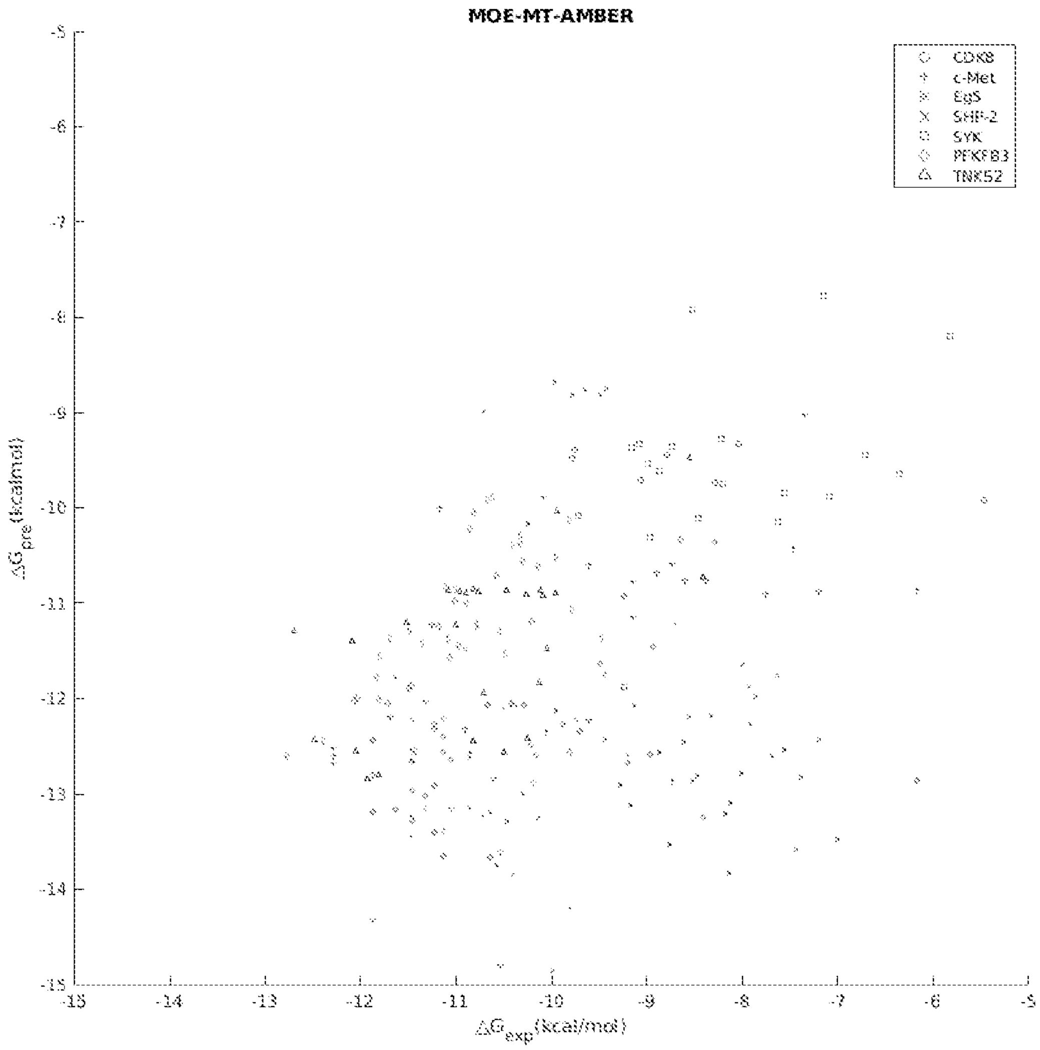
FIG. 8 [Prior Art]
FIG. 8 illustrates the scatter plot of the AMBER molecular force field in free energy calculations of prior art.

The binding free energy calculations for the Merck KgaA test set molecular systems are performed using the molecular force field established by the method proposed in this invention, and the results are compared with the latest version of the AMBER molecular force field (AMBERff19SB). The scatter plot in FIG. 8

Figure 9:
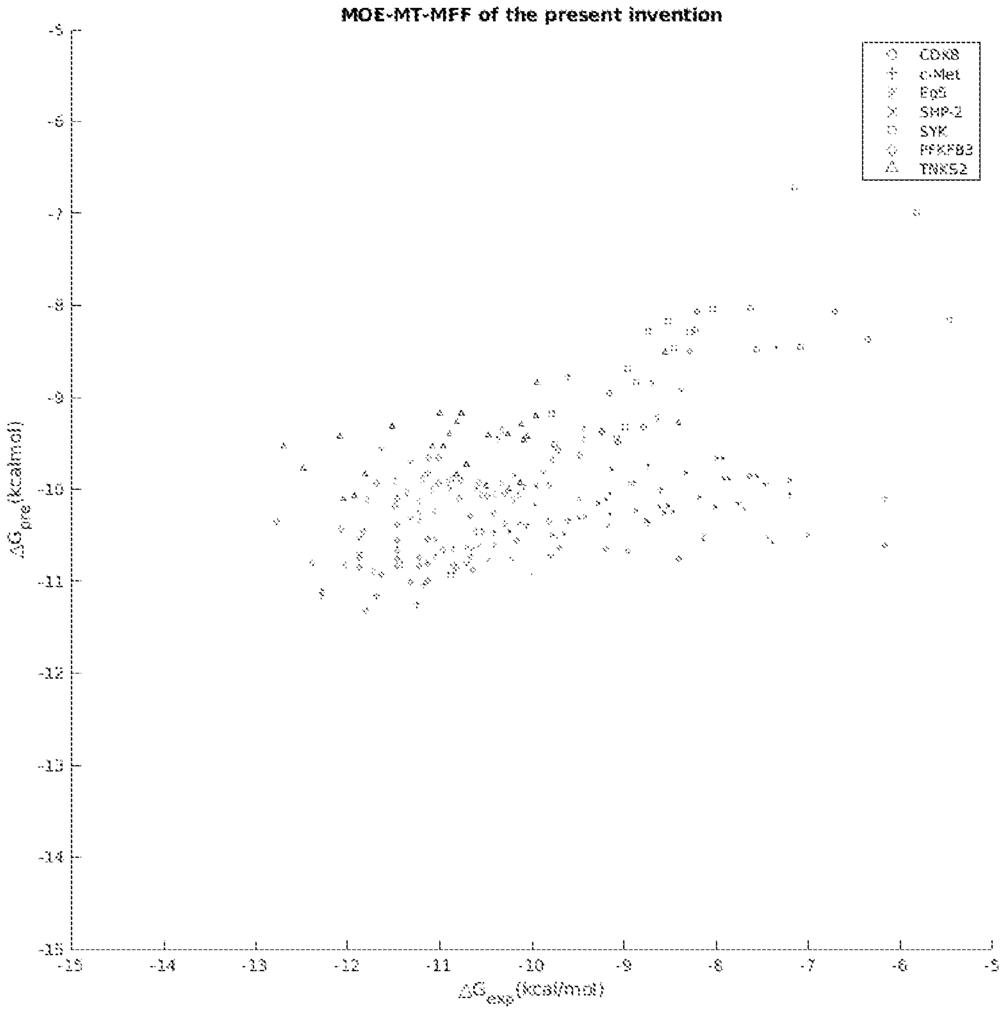
FIG. 9 illustrates the scatter plot of the molecular force field in free energy calculations provided in an embodiment of the present invention.

(AMBERff19SB) and in FIG. 9 (molecular force field of the present invention) illustrate the predicted values versus the experimental values for all samples in the test set, with seven statistical metrics including Pearson correlation coefficient, Kendall correlation coefficient, and Mean Absolute Error (MAE). The molecular force field proposed in the present invention consistently outperforms the AMBERff19SB molecular force field. Particularly noteworthy is the MAE, where the calculations with the AMBER molecular force field yield MAE values exceeding 2 kcal/mol for five test sets, whereas using the method proposed in this patent, the MAE for all test sets is below 2 kcal/mol.

Another embodiment of the present invention also provides a computer-readable storage medium. The computer-readable storage medium stores a computer program that, when executed by a processor, performs the method described above.

Another embodiment of the present invention also provides an electronic device comprising a processor and a memory. The memory stores machine-readable instructions executable by the processor, wherein when the machine-readable instructions are executed by the processor, the method described above is performed.

It should be noted that the various embodiments described in this specification are described in a progressive manner, with each embodiment primarily focusing on the differences from the other embodiments. Common or similar aspects among the various embodiments are cross-referenced accordingly. For device-related embodiments, due to their basic similarity to method embodiments, their descriptions are relatively straightforward. Relevant aspects can be referred to in the description of the method embodiments.

In the several embodiments provided in the present invention, it should be understood that the disclosed devices and methods can also be implemented in other ways. The device embodiments described above are illustrative, and the system architecture, functionality, and operations of devices, methods, and computer program products according to multiple embodiments of the present invention are shown in flowcharts and diagrams in the drawings. Each box in the flowcharts or diagrams may represent a portion of a module, program segment, or code, and a portion of the module, program segment, or code includes executable instructions for implementing specified logical functions. It should also be noted that in some alternative implementations, the functions indicated in the boxes may occur out of the order shown in the drawings. For example, two consecutive boxes can be executed substantially in parallel, and at times they can be executed in the reverse order, depending on the functionality involved.

Additionally, in various embodiments of the present invention, the functional modules of each embodiment can be integrated to form an independent part, or they can exist separately. Furthermore, two or more modules can be integrated to form an independent part. Moreover, in the description of this specification, terms such as "one embodiment," "some embodiments," "examples," "specific examples," "some examples," and the like are intended to include specific features, structures, materials, or characteristics described in conjunction with one or more embodiments or examples included in the embodiments of the present invention. In this specification, the illustrative representations of the above terms do not necessarily refer to the same embodiment or example. Additionally, specific features, structures, materials, or characteristics described can be combined in an appropriate manner in any one or more embodiments or examples. Furthermore, those skilled in the art may combine and mix different embodiments or examples as well as the features of different embodiments or examples, provided they are not mutually contradictory.

The above descriptions are merely optional embodiments of the present invention. However, the scope of protection of the present invention is not limited to these embodiments. Any person skilled in the art familiar with the technical field of the present invention, within the technical scope disclosed in the present invention, may readily contemplate modifications or substitutions, all of which should be encompassed within the scope of protection of the present invention.

We claim:

1. A computer-implemented method for constructing a molecular force field for simulating interatomic interactions of a molecular system, comprising the steps of:

establishing a molecular force field database, comprising a multitude of complex molecules, with each complex molecule being a protein molecule or a ligand molecule, or a combination of one or multiple protein molecules with one or multiple ligand molecules;

conducting homology modeling for each protein molecule with missing amino acid residues to complete the missing amino acid residues;

calculating atomic partial charges by means of quantum mechanics methods, and employing computational molecular dynamics software to achieve dynamic equilibrium states;

classifying atomic types for atoms in the molecular force field database by creating a fingerprint for each atom in each of the multitude of the complex molecules, wherein creating the fingerprint for said each atom comprises:

extracting a structural feature and an energetic feature from each complex molecule in the molecular force field database, the structural feature denoting a set of three-dimensional spatial coordinates of an entirety of the atoms of the complex molecule, the energetic feature denoting a charge distribution of the entirety of the atoms of the complex molecule, the charge distribution comprising partial charge and proton charge;

constructing, for said each atom, a Fibonacci sphere lattice of points uniformly distributed on a spherical surface of said each atom; projecting a gross atom population (GAP) of said each atom onto the points of the Fibonacci sphere lattice based on spatial distances, thereby simulating a charge density distribution on the surface of said each atom;

performing dimensionality reduction and sorting on energy projection values of the points of the Fibonacci sphere lattice, by replacing three-dimensional coordinates of the points with one-dimensional indices of the Fibonacci sphere lattice, to obtain the fingerprint for said each atom;

aggregating a multitude of the atoms belonging to each element from any molecule in the molecular force field database;

clustering, only within the fingerprints of atoms of a same element, the multitude of the fingerprints of the multitude of the atoms belonging to said each element from any molecule in the molecular force field database by a machine learning clustering method; and classifying the atomic types of the multitude of the atoms belonging to said each element via a one-to-one correspondence between each fingerprint and a corresponding atom, whereby atoms sharing a charge density distribution characteristic on their surfaces are classified into a same atomic type; and fitting a molecular force field potential function by means of BFT (Bayesian field theory) in combination with Boltzmann probability distribution.

2. The method for constructing the molecular force field of claim 1, wherein fitting the potential energy function of the molecular force field comprises the steps of:

retrieving a complex molecule as a target molecule from the molecular force field database, the target molecule being a protein-ligand molecule of a combination of two molecules, with a first molecule in the complex molecule being a protein molecule, and a second molecule being a ligand small molecule;

modeling the target molecule employing BFT, obtaining a Boltzmann probability between each pair of the atoms in each atomic ensemble, wherein said each atomic ensemble consisting of either a pair of two atoms or a group of three or more atoms, wherein two atomic ensembles are of different types if and only if at least one atom of one atomic ensemble has an atomic type different from an atomic type of a corresponding atom of the other atomic ensemble, and wherein the Boltzmann probability is a conditional probability determined solely by an interaction energy between the pair of the atoms as determined by mutual interaction thereof; and fitting the Boltzmann probability distribution between said each pair of the atoms in an entirety of the atomic ensembles to obtain the potential energy function between said each pair of the atoms in an entirety of the atomic ensembles.

3. The method for constructing the molecular force field of claim 2, wherein modeling the target molecule employing BFT, obtaining the Boltzmann probabilitydistribution between said each pair of the atoms in said each atomic ensemble comprises the steps of:

for each atomic ensemble of the target molecule, partitioning a molecular system of the target molecule into a core zone and a background zone, wherein the core zone being a region of the molecular system in which said each atomic ensemble is situated, while the background zone being a region of the molecular system minus the core zone; and iteratively removing influence of the atoms in the background zone on the probability density distribution of the atoms of the core zone to obtain a Boltzmann probability between said each pair of atoms in said each atomic ensemble of the target molecule.

4. The method for constructing the molecular force field of claim 1, wherein in said clustering, incorporating into the molecular force field database atomic types unfound in the molecular force field database.

5. The method for constructing the molecular force field of claim 1, wherein the projection employs a Gaussian basis set as a projection function model.

6. One or more non-transitory computer-readable hardware storage device having embedded therein a set of instructions which, when executed by one or more processors of a computer, causes the computer to execute operations comprising:

establishing a molecular force field database comprising a multitude of complex molecules, with each complex molecule being a protein molecule or a ligand molecule, or a combination of one or multiple protein molecules with one or multiple ligand molecules, including conducting homology modeling for each protein molecule with missing amino acid residues to complete the missing amino acid residues, calculating atomic partial charges by means of quantum mechanics methods, and employing computational molecular dynamics software to achieve dynamic equilibrium states;

creating a fingerprint for each atom in each of the multitude of the complex molecules by: extracting a structural feature and an energetic feature from said each complex molecule, the structural feature denoting a set of three-dimensional spatial coordinates of an entirety of atoms of the complex molecule, the energetic feature denoting a charge distribution of the entirety of the atoms of the complex molecule, the charge distribution comprising partial charge and proton charge;

constructing, for said each atom, a Fibonacci sphere lattice of points uniformly distributed on a spherical surface of said each atom;

projecting a gross atom population (GAP) of said each atom onto the points of the Fibonacci sphere lattice based on spatial distances, thereby simulating a charge density distribution on the surface of said each atom;

performing dimensionality reduction and sorting on energy projection values of the points of the Fibonacci sphere lattice to obtain the fingerprint for said each atom;

classifying atoms in the molecular force field database by clustering, only within fingerprints of atoms of a same element, the multitude of the fingerprints of the multitude of the atoms belonging to each element, and classifying atomic types via a one-to-one correspondence between each fingerprint and a corresponding atom;

fitting a molecular force field potential function by means of Bayesian field theory (BFT) in combination with Boltzmann probability distribution; and establishing a molecular force field based on the molecular force field potential function.

7. A system comprising one or more computer processors and a memory storing machine-readable instructions that, when executed by the one or more computer processors, cause the system to perform operations comprising:

establishing a molecular force field database comprising a multitude of complex molecules, with each complex molecule being a protein molecule or a ligand molecule, or a combination of one or multiple protein molecules with one or multiple ligand molecules, including conducting homology modeling for each protein molecule with missing amino acid residues to complete the missing amino acid residues, calculating atomic partial charges by means of quantum mechanics methods, and employing computational molecular dynamics software to achieve dynamic equilibrium states;

creating a fingerprint for each atom in each of the multitude of the complex molecules by: extracting a structural feature and an energetic feature from said each complex molecule, the structural feature denoting a set of three-dimensional spatial coordinates of an entirety of atoms of the complex molecule, the energetic feature denoting a charge distribution of the entirety of the atoms of the complex molecule, the charge distribution comprising partial charge and proton charge;

constructing, for said each atom, a Fibonacci sphere lattice of points uniformly distributed on a spherical surface of said each atom;

projecting a gross atom population (GAP) of said each atom onto the points of the Fibonacci sphere lattice based on spatial distances, thereby simulating a charge density distribution on the surface of said each atom;

performing dimensionality reduction and sorting on energy projection values of the points of the Fibonacci sphere lattice to obtain the fingerprint for said each atom;

classifying atoms in the molecular force field database by clustering, only within fingerprints of atoms of a same element, the multitude of the fingerprints of the multitude of the atoms belonging to each element, and classifying atomic types via a one-to-one correspondence between each fingerprint and a corresponding atom;

fitting a molecular force field potential function by means of Bayesian field theory (BFT) in combination with Boltzmann probability distribution; and establishing a molecular force field based on the molecular force field potential function.

8. The method for constructing the molecular force field of claim 1, wherein the machine learning clustering method comprises a K-means algorithm, a K-means++ algorithm, or an artificial neural network algorithm.

9. The method for constructing the molecular force field of claim 1, wherein the clustering comprises evaluating a clustering result against evaluation criteria comprising a silhouette coefficient greater than 0.9 and a smallest resulting cluster containing a number of samples not less than 5% of a total number of samples, and, when the evaluation criteria are not satisfied, adjusting a number of clusters and repeating the clustering.

10. The method for constructing the molecular force field of claim 1, wherein the Fibonacci sphere lattice comprises N points uniformly distributed on the spherical surface, and N is 1000.

* * * * *